United States Patent [19]

Matsuyama et al.

[11] Patent Number: 6,165,515
[45] Date of Patent: Dec. 26, 2000

[54] METHOD FOR TREATMENT OF OSTEOPOROSIS

[75] Inventors: Toshikatsu Matsuyama, Sapporo; Jin-emon Konishi, Tokyo, both of Japan

[73] Assignee: Nippon Zoki Pharmaceutical Co., Ltd., Osaka, Japan

[21] Appl. No.: 09/099,334

[22] Filed: Jun. 18, 1998

[30] Foreign Application Priority Data

Sep. 12, 1997 [JP] Japan .................................. 9-267988

[51] Int. Cl.$^7$ .......................... A61K 35/00; A61K 35/34; A61K 35/12
[52] U.S. Cl. .......................... 424/520; 424/522; 424/548; 424/553; 424/572
[58] Field of Search .................................. 424/520, 522, 424/548, 553, 557, 572, 574

[56] References Cited

U.S. PATENT DOCUMENTS

| | | | |
|---|---|---|---|
| 3,959,566 | 5/1976 | Pangonis | 428/446 |
| 4,036,787 | 7/1977 | Blount | 528/405 |
| 4,039,474 | 8/1977 | Feistel et al. | 502/8 |
| 4,056,937 | 11/1977 | Suzuki | 405/264 |
| 4,089,883 | 5/1978 | Blount | 536/107 |
| 4,138,421 | 2/1979 | Blount | 556/443 |
| 4,863,518 | 9/1989 | Blount | 106/634 |
| 4,985,254 | 1/1991 | Konishi et al. | 424/520 |
| 4,985,354 | 1/1991 | Toyomaki et al. | 435/13 |
| 5,013,558 | 5/1991 | Konishi | 424/520 |
| 5,057,324 | 10/1991 | Shibayama et al. | 424/520 |
| 5,127,994 | 7/1992 | Johansson | 162/168.3 |
| 5,227,089 | 7/1993 | Hasegawa et al. | 252/181 |
| 5,534,509 | 7/1996 | Konishi et al. | 514/210 |
| 5,560,935 | 10/1996 | Konishi et al. | 424/520 |
| 5,658,896 | 8/1997 | Konishi et al. | 514/63 |
| 5,807,951 | 9/1998 | Konishi et al. | 527/300 |

FOREIGN PATENT DOCUMENTS

| | | |
|---|---|---|
| 0 733 636 A1 | 9/1966 | European Pat. Off. . |
| 0 300 973 | 4/1989 | European Pat. Off. . |
| 0 315 591 | 10/1989 | European Pat. Off. . |
| 0 341 209 | 11/1989 | European Pat. Off. . |
| 0 621 038 A1 | 10/1994 | European Pat. Off. . |
| 0 645 142 A1 | 3/1995 | European Pat. Off. . |
| 2 610 523 | 8/1988 | France . |
| 2 671 488 | 7/1992 | France . |
| 53-101515 | 9/1978 | Japan . |
| 57-77697 | 4/1980 | Japan . |
| 58-351117 | 8/1981 | Japan . |
| 3-204803 | 9/1981 | Japan . |
| 57-183720 | 11/1982 | Japan . |
| 58-121217 | 7/1983 | Japan . |
| 62-145022 | 6/1987 | Japan . |
| 63-25600 | 5/1988 | Japan . |
| 63-039572 | 8/1988 | Japan . |
| 3-43279 | 7/1991 | Japan . |
| 2594222 | 12/1996 | Japan . |
| 697351 | 9/1953 | United Kingdom . |

OTHER PUBLICATIONS

Chemical Abstracts, vol. 106, No. 10, Mar. 9, 1987, Srivastava et al., XP002096181.

Patent Abstracts of Japan, vol. 017, No. 225 (C–1055), May 10, 1993 & JP 04360838.

Database WPI Section Ch, Week 9624, Derwent, XP002113090 & CN 1 096 180, Dec. 14, 1994, abstract.

Database BIOSIS, XP–002113089, Li S–Y, et al. Studies on the Protective Action of Silicon Compound of Equisetum Against Experimental Liver Injury in Rats and Mice & Zhongguo Yaolixue Yu Dulixue Zazhi. ISSN; 1000–3002, abstract.

Zhao C, et al., "Determination of water soluble silicon from herbal drugs", Chung Kuo Chung Yao Tsa Chih, vol. 15, No. 9, 1990, pp. 555–556.

Paslawska et al., "Studies on the Optimum Conditions of Extraction of Silicon Species from Plants With Water", Planta Medica, vol. 29, No. 1, 1976, pp. 72–79, & XP002113087.

Piekos et al., "Studies on the Optimum Conditions of Extraction of Silicon Species from Plants With Water", Planta Medica, vol. 27, 1975, pp. 145–150, XP002113088.

Database WPI, Section Ch, Week 9411, Derwent, XP002113091 & RU 2003338 C, Nov. 30, 1993, abstract.

Patent Abstracts of Japan, vol. 014, No. 254 (C–0724), May 31, 1990 & JP 02073020, abstract.

"Drug for Food Poisoning," *Patent Abstracts of Japan*, vol. 11, No. 371 (C–462), Dec. 3, 1987 & JPA62145022 (Sofuto Shirika) Jun. 29, 1987, abstract.

"Adsorbent For Peroxylipid," *Patent Abstracts of Japan*, vol. 15, No. 474 (C–890), Dec. 3, 1991 & JPA3204803 (Shiscido Co., Ltd.) Sep. 6, 1991, abstract.

The Merck Index, 9th ed. 1976, No. 7456, 8443, 8233–8243 & 5514–5515.

Fujii, Y., et al., "Biological Overview of HIV Accessory Protein Nef," *Saibo Kogaku*, vol. 16, No. 1, pp. 94–99 (1997).

(List continued on next page.)

*Primary Examiner*—Ali Salimi
*Attorney, Agent, or Firm*—Hollander Law Firm, P.L.C.

[57] ABSTRACT

A therapeutic agent for osteoporosis brought about by a decrease in estrogen comprises an extract from inflammatory rabbit skin inoculated with vaccinia virus as an effective component. In ovariectomized rats, a model animal for osteoporosis brought about by a decrease in estrogen, the extract from inflammatory rabbit skin inoculated with vaccinia virus has an excellent action for maintaining bone volume and bone strength. The therapeutic agent containing the extract as an active component is very useful for treatment and prevention of osteoporosis brought about by a decrease in estrogen which is frequently caused by menopause or ovariectomy in women. The extract from inflammatory rabbit skin inoculated with vaccinia virus has a high safety profile even when administered for a long term.

20 Claims, No Drawings

OTHER PUBLICATIONS

Derwent Publications Ltd., London, GB: AN 82–10241J, "Drug for Cultivated Fish," & JP A57183720 (Mitani J.), Nov. 12, 1982, abstract.

Abbasi–Jahromi et al., "Bone Quality Factor Analysis: A New Noninvasive Technique for the Measurement of Bone Density and Bone Strength," *Journal of Bone and Mineral Research*, vol. 11, No. 5, 1996, pp. 594–599.

Richards, et al., "Normal Age–Related Changes in Fluoride Content of Vertebral Trabecular Bone—Relation to Bone Quality," *Bone*, vol. 15, No. 1, 1994, pp. 21–26.

Sogaard, et al., "A Comparison of the Effects of Two Anabolic Agents (Fluoride and PTH) on Ash Density and Bone Strength Assessed in an Osteopenic Rat Model," *Bone*, vol. 20, No. 5, May 1997: 439–449.

Ke et al., "Prostaglandin $E_2$ Increases Bone Strength in Intact Rats and in Ovariectomized Rats With Established Osteopenia," *Bone*, vol. 23, No. 3, Sep. 1998:249–255.

Takenoka, t. et al, "Influence of Neuroptropin on Thymic Microenviromental Abnormalities of NZB Mice", Int. J. Immunotherapy, XI(2), pp. 49–56 (1995).

"Drugs in Japan, Ethical Drugs", Yagkugo Jihlo Co., Ltd, 1994, p. 1, 434.

Yokoi, et al., "Effect of Degree of Polymerization of Silicic Acid on the Gastrointestinal Absorption of Silicates in Rats", Chem. Pharm. Bull., vol. 27, No. 8, 1979, pp. 1733–1739.

METHOD FOR TREATMENT OF OSTEOPOROSIS

FIELD OF THE INVENTION

The present invention relates to a therapeutic agent for osteoporosis brought about by a decrease in estrogen, which has a high safety profile even when administered for a prolonged period of time.

BACKGROUND OF THE INVENTION

As the segment of the population advanced in age increases in society, the number of patients with osteoporosis is rapidly increasing. The diagnostic criteria and therapy for osteoporosis have been earnestly investigated. Bones become friable and weak in the osteoporosis patient. Pressure fracture of the spine and limb fracture causing pain or dysfunction to the patient easily occur by a trifle action or weak impact. Osteoporosis not only imparts pain to the patient but often makes the patient bedridden, leading to heavy burdens upon persons attending to the patient and to society supporting medical expenses.

Various pathophysiologies of osteoporosis have been suggested. Osteoporosis in women rapidly increases after menopause and the early onset of osteoporosis is observed in ovariectomy women. Accordingly, a decrease in female hormones, especially estrogen, is thought to be the important cause of osteoporosis. In fact, the occurrence of osteoporosis in women is several times that in men. Also, osteoporosis in women occurs earlier than in men and its occurrence rapidly increases around menopause. Osteoporosis brought about by the decrease in estrogen is the leading cause of the disease and is one of the diseases for which an appropriate therapeutic agent has been sought. The first choice for the treatment of osteoporosis in Europe and America is estrogen replacement therapy to replenish estrogen. However, estrogen causes undesirable side effects such as metrorrhagia and mammary hypertrophy. Estrogen replacement therapy also has a high risk of inducing mammary carcinoma. Therefore, estrogen replacement therapy in Japan is not preferred unlike as in Europe and America.

Since the estrogen replacement therapy against osteoporosis may have adverse side effects, a drug with a much higher safety profile than estrogen replacement therapy and which can be administered for a long term is needed.

The inventors of the present invention have found that an extract from inflammatory rabbit skin inoculated with vaccinia virus has superior effects for treatment of osteoporosis accompanied by a decrease in estrogen, such as maintaining bone volume, trabecular connectivity and bone strength.

SUMMARY OF THE INVENTION

The present invention provides a therapeutic agent for osteoporosis brought about by a decrease in estrogen which comprises an extract from inflammatory rabbit skin inoculated with vaccinia virus as an effective component.

DETAILED DESCRIPTION OF THE INVENTION

The present invention provides a method for treating and preventing osteoporosis which results from a decrease in estrogen, which may be caused by menopause or ovariectomy in women. Treatment and prevention of accelerated bone resorption and inhibition of a decrease of bone volume, bone quality and bone strength is also provided by the present invention. In accordance with the methods of the present invention, a pharmaceutical composition containing an extract from inflamed tissue as an effective component may be used to maintain or increase bone volume, bone quality, and bone strength. Trabecular connectivity and trabecular unconnectivity may be maintained at healthy levels with the pharmaceutical compositions of the present invention. Osteoporosis and its symptoms such as decreased bone volume, bone quality, and bone strength, decreased trabecular connnectivity, and increased trabecular unconnectivity may be treated or prevented by administration of a pharmaceutically effective amount of the extract to a patient in need thereof.

The effective component of the pharmaceutical composition of the present invention is a non-protein biofunction-regulating substance extracted from inflammatory tissues inoculated with vaccinia virus. The tissue which is inoculated may be human or animal tissue, such as tissue of a mammal, for example skin tissue of a rabbit or other mammal. A commercially available drug preparation of an extract from inflammatory rabbit skin inoculated with vaccinia virus is sold in Japan under the trade name Neurotropin by Nippon Zoki Pharmaceutical Co., Osaka, Japan. As mentioned at page 1,434 of "Drugs in Japan, Ethical Drugs" (published in August of 1994; edited by Japan Pharmaceutical Information Center; published by Yakugyo Jiho Co., Ltd.), this preparation is a drug containing a non-protein active substance extracted and isolated from inflammatory tissues of rabbits inoculated with vaccinia virus. The preparation has been allowed for treatment of lower back pain, neck-shoulder-arm syndromes, periarthritis scapulohumeralis, osteoarthritis, symptomatic neuralgia, itching accompanied with skin disorders (such as eczema, dermatitis and urticaria), allergic rhinitis, sequelae of subacute myelo-optico-neuropathy (such as coldness, pain and paresthesia/dysesthesia), etc. It is approved as an ethical drug in the form of injections (subcutaneous, intramuscular and intravenous) and tablets, and is commercially available.

Neurotropin was used in an experimental study at the School of Medicine, University of California, Davis, to evaluate its influence on thymic microenvironmental abnormalities of New England black mice as reported by Y. Takeoka et al, *Int. J Immunotherap*, XI(2), pp. 49–56 (1995). As taught by Takeoka et al, Neurotropin is a non-protein extract isolated from the inflamed dermis of rabbits inoculated with vaccinia virus and it has been reported in the literature as: 1) having beneficial effects on immune-depressed animals, 2) clinically useful as an analgesic and as an anti-allergy drug with few side-effects in humans, 3) improving the immune status of murine lupus in (NZB/NZW) F1 mice, and 4) inhibiting the development of EAE in Lewis rats, an autoimmune model of human multiple sclerosis.

The commercially available extract, Neurotropin, may be used in the compositions and methods of the present invention. The descriptions, properties and dosages of Neurotropin reported in the above-mentioned "Drugs in Japan, Ethical Drugs" and the Takeoka et al article are incorporated herein by reference in their entireties.

In addition, extracts from inflammatory tissue inoculated with vaccinia virus disclosed in Japanese Examined Patent Publications Sho-63/039,572 B, Sho-63/025,600 B and Hei-03/043,279 B and U.S. Pat. Nos. 5,013,558 to Konishi and 5,560,935 to Konishi, et al. can be utilized as the active substance of the present invention. The extract manufacturing methods and preferred doses for use herein are also illustrated in said references. The disclosures of Japanese Examined Patent Publications Sho-63/039,572 B, Sho-63/025,600 B and Hei-03/043,279 B, and U.S. Pat. Nos. 5,013,558 to Konishi and 5,560,935 to Konishi, et al. are herein incorporated by reference in their entireties.

A method for producing an extract from inflammatory tissue inoculated with vaccinia virus for use in the present invention is described, for example, in Example 1 of Japanese Examined Patent Publication Sho-63/039,572 B. As disclosed therein, vaccinia virus is inoculated to the skin of healthy adult rabbit. The inflamed skin is cut off under aseptic conditions and well ground. Aqueous phenol-added glycerol solution is added to this ground material and subjected to homogenization, and the emulsion is filtered by centrifugation. The resulting filtrate is adjusted to about pH 4.8–5.5, and then heated in a stream of 100° C. steam. After removing proteins thereby precipitated by filtration, the filtrate is adjusted to about pH 9.2 by addition of sodium hydroxide, heated at about 100° C. and filtered. The filtrate is adjusted to about pH 4.5 by addition of hydrochloric acid, and about 1.5% active carbon is added thereto. After stirring for about 1.5 hours, the suspension is filtered. Water is added to the resulting active carbon and the suspension is adjusted to pH 9.4–10 by addition of sodium hydroxide. The extraction procedure is carried out by stirring for about 3–5 hours. The suspension is filtered to remove the active carbon. The filtrate is adjusted to about pH 7.0–7.2 by addition of hydrochloric acid and concentrated to dryness under reduced pressure to give the extract of the present invention in a yield of about 1.5–2 g per 1 kg infected skin-tissues.

In the method of Japanese Examined Patent Publication Sho-63/025,600 B, which may be employed to produce an extract for use in the present invention, various kinds of animal tissue infected with pox obtained by inoculating a pox virus into the animals is ground, and extracted with an extracting solvent to remove a portion. The extracted solution is brought into contact with an adsorbent under acidic conditions and the adsorbed substance is eluted with water, etc. The eluate is converted into an aqueous solution, which is brought into contact with an adsorbent under acidic conditions, the adsorbed substance is eluted with a weakly basic organic solvent, etc., and the solvent is removed to give a physiologically active substance. The substance extracted from animal tissue in pox, is a light yellowish brown amorphous hygroscopic powder, soluble in water and methanol, insoluble in benzene and ether, and has a pH of 6.5–7.5, and ultraviolet absorbance of $\lambda max = 265-275$ nm. It is positive in color reaction in the ninhydrin reaction, orcinol hydrochloric acid reaction, and arsenic molybdic acid method, and is negative in detection reactions for various kinds of protein.

In the method of Japanese Examined Patent Publication Hei-03/043,279 B, which may be employed to produce an extract for use in the present invention, sterilely collected tissues with poxes are ground, combined with phenol-water in an amount of 1–5 times that of the tissue to form a milk-like substance, then subjected to filtration or centrifugation. The resultant solution is adjusted in pH near its isoelectric point, heated, filtered to remove protein and made acidic with a mineral acid, then adsorbed on 5–20% activated carbon. The activated carbon is combined with an aqueous alkali to adjust its pH to 10–12, and exudation is effected under heating. The exudate is evaporated to dryness under reduced pressure or freeze dried to give the physiologically active substance.

Methods for producing extracts from inflammatory tissue inoculated with vaccinia virus for use in the present invention are also described, for example, in U.S. Pat. No. 5,013,558 to Konishi at column 1 line 44 to column 3 line 22, and in Examples 1 and 2 at column 3 lines 33 to 62, and U.S. Pat. No. 5,560,935 to Konishi, et al. at column 2 line 55 to column 3 line 14, and column 3 line 33 to column 4 line 64, and in Examples 1 and 2 at column 5 line 6 to column 6 line 8, which are herein incorporated by reference in their entireties.

Thus, in accordance with the manufacturing method of U.S. Pat. No. 5,013,558 to Konishi, an extract from inflammatory tissue inoculated with vaccinia virus for use in the present invention may be prepared as follows:

(1) Inflamed or infected tissues are homogenized with an extraction medium, and tissue fragments are removed.

(2) The extracted solution thus obtained is subjected to treatment to remove proteins.

(3) An adsorbent is added to the deproteinized solution, and then the material adsorbed onto the adsorbent is eluted.

Inflamed or infected tissues may be animal tissues, organs or cultured cells inoculated or infected with vaccinia virus, a poxvirus.

To obtain the infected tissues, various kinds of animals or birds can be utilized, for example, rabbit, sheep, goat, pig, cow, horse, monkey, hamster, guinea pig, rat, mouse or hen can be employed. Also any kind of cultured cell, in which the vaccinia virus can multiply, for example, cultured cell or tumor cell of kidney, skin, lung, testis, liver, muscle, adrenal, thyroid gland, brain, nerve cell or blood cell of rabbit, sheep, goat, pig, cow, horse, monkey, hamster, guinea pig, rat, mouse, hen or their embryo, cultured cell derived from humans such as Hela cell, or decidua of the hatching egg can be employed.

The inflamed or infected tissues are collected under aseptic conditions and may be ground to as small a size as possible. An extraction medium is added to the ground material which is then homogenized. As an extraction medium, distilled water, physiological saline, weakly acidic or basic buffer, etc. may be used. A stabilizer such as glycerin, a disinfectant or preservative such as phenol, or an inorganic salt such as sodium chloride, potassium chloride or magnesium chloride can be added to the medium. At that time, the extraction can be facilitated by a procedure to disintegrate cell tissues, such as freeze-thaw extraction, sonication or treatment with a detergent or an enzyme for dissolving cell membrane.

The resulting emulsion is filtered or centrifuged to remove tissue fragments. The filtrate or supernatant is deproteinized which can be carried out according to a known method, for example, heating, sonication, treatment with a protein-denaturant such as an acid, a base, urea, guanidine, an organic solvent or a detergent, isoelectric point precipitation or salting-out technique. Subsequently, the denatured proteins thereby precipitated are removed by filtration using a filter paper such as cellulose or nitrocellulose, a glass filter, sellaite, Seitz's filter etc., ultrafiltration, gel filtration, ion-exchange chromatography or centrifugation.

The resulting extract containing the active substances is acidified, preferably to pH 3.5–5.5, by addition of an acid such as hydrochloric acid, sulfuric acid or hydrobromic acid, and then subjected to adsorption to an adsorbent such as activated carbon, kaolin or an ion-exchange resin. The adsorbent can be added to the extracted solution and stirred, or the extracted solution can be passed through a column of the adsorbent.

To elute the material containing the active substances of the present invention, a basic solution is added to the adsorbent, preferably adjusting the suspension to pH 9–12, and then the mixture is incubated or stirred at room temperature or at a suitable temperature above room temperature by heating. The elution is achieved by removing the absorbent according to a known method such as filtration or centrifugation. The eluate thus obtained, preferably after adjusting it to pH 6.5–8.5, may be concentrated to dryness under reduced pressure or lyophilized to give the extracted active substances of the present invention.

The physical and chemical properties of the physiologically active extract obtained in the above preparation are:

(1) Appearance: Pale yellowish brown and hygroscopic powder.

(2) Solubility: Soluble in water, methanol and ethanol.

(3) Ultraviolet adsorption: $\lambda$max=255–275 nm.

(4) Ninhydrine reaction: Positive.

(5) Orcinol-iron (III) chloride-hydrochloric acid method: Positive. For example, one ml of perchloric acid is added to 2 mg of the extract of the present invention, and is heated until the solution become colorless. 3 ml of dilute hydrochloric acid, 0.4 g of amidol hydrochloride and 8 g of sodium hydrogen sulfite are dissolved in 100 ml of water, and then 2 ml of the resulting aqueous solution, 1 g of ammonium molybdate and 30 ml of water are mixed. 2 ml of the mixture is added to the above solution containing the extract of the present invention. Finally, the solution shows a blue color.

(6) Molybdenum blue method: Positive. For example, 5 mg of the extract of the present invention is dissolved in 10 ml of water, 0.2 g of orcine and 0.135 g of iron(II) ammonium sulfate are dissolved in 5 ml of ethanol, 83 ml of hydrochloric acid is added to the mixture, and water is added until the total becomes 100 ml. 3 ml of the resulting mixture is added to 1 ml of the above solution containing the extract of the invention and heated in a boiling water bath. Finally, the solution shows a green color.

(7) Silver nitrate reagent is added to an aqueous solution of the extract of the present invention and a precipitate is produced.

(8) Contains nucleic acid bases.

(9) Various methods of protein detection are negative.

An extract from inflammatory tissue inoculated with vaccinia virus for use in the present invention prepared in accordance with the manufacturing method of U.S. Pat. No. 5,560,935 to Konishi, et al., as disclosed therein may contain silicon components which are water-soluble silicic acids, water-soluble silicates, polymers of water-soluble silicic acids, polymers of water-soluble silicates, or mixtures thereof. For example, the silicon components may be present as one or more silicic acids such as orthosilicic acid, metasilicic acid, mesodisilicic acid, mesotrisilicic acid, mesotetrasilicic acid, etc. or one or more alkali salts (e.g. sodium and potassium salts) thereof They may be present in the form of monomers or in a polymerized form. The physiologically active extract contains 1–20 micrograms/mg (preferably 1.5–15 micrograms/mg) of the silicon components when calculated as silicon.

An extract prepared in accordance with U.S. Pat. No. 5,650,935 may be an amorphous and hygroscopic powder with a pale yellowish brown color containing 1 to 20 micrograms/mg (e.g. 2 to 10 micrograms/mg) of at least one silicon component calculated as silicon and having:

1. solubility in water, methanol and ethanol but insolubility in benzene and ether,
2. a pH of 6.0 to 8.3,
3. an ultraviolet absorption of $\lambda$max=265 to 275 nm, and
4. color reactions: amino acids (positive to a ninhydrin reaction), sugars (positive to an orcinol-iron (III) chloride-hydrochloric acid method), phosphorus (positive to a molybdenum blue method), proteins (negative to a trichloroacetic acid method) and phenols (negative to a ferric chloride method).

With regard to the route of administration to the patient, subcutaneous, intramuscular and intravenous administrations by injection and oral administration by tablets are approved for the commercially available agent and may be used herein. However, it is also possible to administer pharmaceutical dosage forms other than the above-mentioned ones which are optimum for the therapy depending upon the type of the disease. The dose may depend upon the kind of extract from inflammatory tissue inoculated with vaccinia virus. The dose which is approved for the commercially available preparation according to the above "Drugs in Japan, Ethical Drugs" (page 1,434) is, principally, 16 Neurotropin units per day and 3.6–7.2 Neurotropin units per day by oral administration and by injection, respectively. The approved dose may be employed for the treatments of the present invention. However, the dose may be appropriately increased or decreased depending upon the type of the disease, degree of seriousness, individual difference in the patients, method of administration, period of administration, etc.

An extract from inflammatory tissue inoculated with vaccinia virus which is the effective component of the pharmaceutical compositions of the present invention can be made into various pharmaceutical compositions or preparations by combining one or more of the extracts with at least one pharmaceutical carrier or diluent. The extracts can be made into various types of preparations by known methods. The pharmaceutical preparations or compositions may be made into solid, semi-solid, liquid or aerosol formulations for oral administration (e.g. tablets, capsules, powders, liquids, etc.) and for parenteral administration (e.g. for subcutaneous, intravenous, intramuscular, intrarectal and intranasal administrations).

The extracts of the present invention may be used either solely or jointly in pharmaceutically effective amounts for treating animals or humans. They may also be used in pharmaceutically effective amounts in combination with pharmaceutically effective amounts of other pharmaceutically active components in pharmaceutical compositions or preparations.

In the case of parenteral administration using injections, for example, it is possible to prepare solutions or suspensions of one or more extracts of the present invention in pharmaceutically acceptable carriers such as aqueous and nonaqueous solvents such as distilled water for injection, physiological saline solution, Ringer's solution, plant oil, synthetic fatty acid glycerides, higher fatty acid esters, propylene glycol, etc.

In the case of preparations for oral administration, one or more of the extracts of the present invention alone or together with commonly-used pharmaceutically acceptable excipients in pharmaceutically acceptable amounts such as a suitable pharmaceutically acceptable additive or carrier (e.g. lactose, mannitol, corn starch, potato starch, etc.) may be mixed with one or more pharmaceutically acceptable: (1) binders such as crystalline cellulose, cellulose, cellulose derivatives, gum arabicum, corn starch, gelatin, etc., (2) disintegrating agents such as corn starch, potato starch, potassium carboxymethyl-cellulose, etc., (3) lubricating agents such as talc, magnesium stearate, etc., and (4) other pharmaceutically acceptable excipients including pharmaceutically acceptable bulking agents, moisturizing agents, buffers, preservatives, perfumes and the like to obtain tablets, diluted powders, granules or capsules.

It is also possible, depending upon the type of the disease, to prepare pharmaceutical preparations other than the above-mentioned ones such as suppositories, inhalations, aerosol preparations, collyriums, ointments, poultices, etc.

For example, suppositories may be prepared by mixing at least one extract of the present invention with pharmaceutically acceptable amounts of one or more pharmaceutically acceptable fatty/oily bases (e.g. cacao butter), emulsified bases, water-soluble bases (e.g. Macrogol), hydrophilic bases, etc.

In the case of inhalations or aerosol preparations, at least one extract of the present invention in the form of a liquid or minute powder can be filled up in an aerosol container with a gas or liquid spraying agent, and if desired, with conventional adjuvants such as one or more pharmaceutically acceptable humidifying agents or dispersing agents. They can also be used as pharmaceuticals for a non-pressurized preparation such as in a nebulizer or an atomizer.

In order to make the extracts of the present invention into collyriums, they can be prepared as a solution or suspension together with an aqueous solvent such as sterile, purified water and physiologically saline solution, or a non-aqueous solvent for injection. The collyriums may also include pharmaceutically acceptable preservants, sterilizing agents, pH adjusting agents, and the like.

The present invention is further illustrated by the following non-limiting examples wherein all parts, percentages and ratios are by weight, all temperatures are in ° C., and all reactions are conducted at about atmospheric pressure unless indicated to the contrary:

EXAMPLE 1

Pharmacological tests demonstrating the pharmacological action and therapeutic effects of an extract from inflammatory rabbit skin inoculated with vaccinia virus upon osteoporosis brought about by a decrease in estrogen are:

(1) PRODUCTION OF THE EXTRACT

An extract from inflammatory rabbit skin inoculated with vaccinia virus prepared by the manufacturing method described in Example 1 of Japanese Examined Patent Publication Sho-63/039,572 B, said method being herein incorporated by reference, was used in the pharmacological tests.

In accordance with the manufacturing method described in Example 1 of Japanese Examined Patent Publication Sho-63/039,572 B, vaccinia virus is inoculated to the skin of healthy adult rabbit. The inflamed skin is cut off under aseptic conditions and well ground. Aqueous phenol-added glycerol solution is added to this ground material and subjected to homogenization, and the emulsion is filtered by centrifugation. The resulting filtrate is adjusted to about pH 4.8–5.5, and then heated in a stream of 100° C. steam. After removing proteins thereby precipitated by filtration, the filtrate is adjusted to about pH 9.2 by addition of sodium hydroxide, heated at about 100° C. and filtered. The filtrate is adjusted to about pH 4.5 by addition of hydrochloric acid, and about 1.5% active carbon is added thereto. After stirring for about 1.5 hours, the suspension is filtered. Water is added to the resulting active carbon and the suspension is adjusted to pH 9.4–10 by addition of sodium hydroxide. The extraction procedure is carried out by stirring for about 3–5 hours. The suspension is filtered to remove the active carbon. The filtrate is adjusted to about pH 7.0–7.2 by addition of hydrochloric acid and concentrated to dryness under reduced pressure to give the extract of the present invention in a yield of about 1.5–2 g per 1 kg infected skin-tissues.

(2) TEST METHODS

Ovariectomized rats were used to test the pharmacological effectiveness of the extract for the treatment and prevention of osteoporosis. They have been widely utilized as model animals for osteoporosis accompanied by the decrease of estrogen. Forty Wistar rats (6 months old) were divided into four groups as follows:

(1) Sham group (Sham-operated group)

(2) OVX group (Ovariectomized group)

(3) OVX+20 group (Ovariectomized group administered with 20 mg/kg, body weight, of the extract)

(4) OVX+50 group (Ovariectomized group administered with 50 mg/kg, body weight, of the extract).

Rats were either ovariectomized or sham-operated. In the sham-operated group, as is known in the art, control rats are operated upon by surgery as are ovariectomized rats, however the ovary is not cut off. Thus, since the ovariectomized rats suffer pain, etc. from the ovariectomy operation, the control rats are placed in the same condition as the ovariectomized rats by the "sham operation." One week after the operation, the rats were injected simultaneously three times a week for twelve weeks, and all animals were then sacrificed. Blood chemistry, body weight and organ weight were measured and compared among the four groups. Also, bone mineral density (BMD) of the lumbar spine at L2–L5 was measured according to the DXA method using an ODR 1000W (Hologic Inc.). After removing soft tissue, an undecalcified bone sample of the third lumbar vertebral body (L3) was prepared, and kinetic metabolism and two-dimensional strut analysis were measured by bone histomorphometry. Maximum stress (Max S) of the lumbar spine was measured by an L4 compression test.

(3) TEST RESULTS

Compared to the Sham group, the OVX group showed a significant increase of body weight and serum alkaline phosphatase. However, serum calcium level, serum phosphorus level, lumbar spinal BMD and organ weights of liver, kidney and spleen did not show significant differences among the four groups. In histomorphometrial parameters, the OVX group showed a decrease of BV/TV (trabecular bone volume) and NdNd/TSL (trabecular connectivity), and an increase of OS/BS (bone formation), ES/BS (bone resorption) and TmTm/TSL (trabecular unconnectivity) compared with that of the Sham group. Max S of the OVX group significantly decreased in comparison with the Max S of the Sham group. On the other hand, compared to the OVX group, both the OVX+20 and the OVX+50 groups, drug administered groups, did not show the substantial decrease of BV/TV as was shown by the Sham group. In comparison with the Sham group, OS/BS of said drug administered groups increased as well as that of the OVX group. The OVX+20 and OVX+50 groups maintained ES/BS, NdNd/TSL, TmTm/TSL and Max S at a similar level to that of the Sham group.

Detailed results of the tests are shown in Tables 1 and 2. Each value represents the mean ± S.E. The * denotes a statistically significant difference ($p<0.05$) between the Sham group and other groups. The # denotes a statistically significant difference ($p<0.05$) between the OVX group and the drug administered groups. The meanings of each parameter are:

BV/TV: trabecular bone volume (parameter of bone volume)

OS/BS: osteoid surface (parameter of bone formation)

ES/BS: eroded surface (parameter of bone resorption)
NdNd/TSL: node-to-node/total strut parameters (parameter of trabecular connectivity)
TmTm/TSL: free-end-to-free-end/total strut parameters (parameter of trabecular unconnectivity)

TABLE 1

| Group | Bone Volume BV/TV (%) | Bone Formation OS/BS (%) | Bone Resorption ES/BS (%) |
|---|---|---|---|
| Sham group | 27.4 ± 1.7 | 22.8 ± 0.7 | 21.9 ± 1.2 |
| OVX group | 22.2 ± 1.3* | 44.8 ± 2.6* | 29.1 ± 1.1* |
| OVX + 20 group | 25.5 ± 1.4# | 45.8 ± 4.7* | 20.6 ± 1.2# |
| OVX + 50 group | 25.1 ± 2.0# | 48.7 ± 1.7* | 20.0 ± 0.9# |

TABLE 2

| Group | Trabecular Connectivity NdNd/TSL (%) | Trabecular Unconnectivity TmTm/TSL (%) |
|---|---|---|
| Sham group | 51.7 ± 8.0 | 16.5 ± 4.1 |
| OVX group | 26.4 ± 4.8* | 28.7 ± 6.9* |
| OVX + 20 group | 40.2 ± 6.4# | 15.3 ± 2.2# |
| OVX + 50 group | 42.2 ± 4.6# | 13.7 ± 2.0# |

(4) EFFECT OF THE INVENTION

As shown by the above-mentioned results of pharmacological tests, an extract from inflammatory rabbit skin inoculated with vaccinia virus of the present invention inhibited the acceleration of bone resorption resulting from ovariectomy, and also showed an inhibitory action against a decrease of bone volume and bone strength. Recently, it has been indicated that the bone strength not only depends on bone volume but also bone quality. See "Assessment of bone quality by histomorphometry," The Bone, vol. 10, no. 4, pp. 51–60 (1996). As an indication of bone quality, trabecular connectivity dramatically decreased and trabecular unconnectivity dramatically increased in ovariectomized rats. For these changes of bone quality, the extract from inflammatory rabbit skin inoculated with vaccinia virus showed an effect of maintaining the connectivity and unconnectivity at a similar level to that of the Sham group.

As mentioned above, in ovariectomized rats of model animals for osteoporosis brought about by a decrease in estrogen, the extract from inflammatory rabbit skin inoculated with vaccinia virus has an excellent action for maintaining bone volume and bone strength. Therefore, a therapeutic agent of the present invention containing the extract as an active component is very useful for treatment and prevention of osteoporosis brought about by a decrease in estrogen which is frequently caused by menopause or ovariectomy in women. Since the extract from inflammatory rabbit skin inoculated with vaccinia virus is an extracted component from a living body, the extract has a high safety profile with less side effects. Therefore, the drug of the present invention is very useful as a remedy for osteoporosis, a condition for which a drug should be administered for a long term.

We claim:

1. A method for treatment of osteoporosis caused by or accompanying a decrease in estrogen in a patient in need of such treatment comprising administering to said patient a pharmaceutically effective amount of an extract from inflammatory tissue inoculated with vaccinia virus, wherein said extract is a protein free hygroscopic powder, has an ultraviolet adsorption max of 255–275 nm, and is positive for ninhydrin reaction.

2. A method as claimed in claim 1 wherein said patient is treated for osteoporosis caused by or accompanying a decrease in estrogen resulting from menopause.

3. A method as claimed in claim 1 wherein said patient is treated for osteoporosis caused by or accompanying a decrease in estrogen resulting from ovariectomy.

4. A method as claimed in claim 1 wherein the inflammatory tissue is a skin tissue.

5. A method as claimed in claim 4 wherein the inflammatory tissue is a skin tissue of a mammal.

6. A method as claimed in claim 1 wherein the inflammatory tissue is rabbit skin.

7. A method as claimed in claim 1 wherein said extract is administered by injection.

8. A method as claimed in claim 1 wherein said extract is administered orally.

9. A method for maintaining or increasing bone volume, bone quality, or bone strength in a patient afflicted with osteoporosis caused by or accompanying a decrease in estrogen comprising administering to said patient in need thereof a pharmaceutically effective amount of an extract from inflammatory tissue inoculated with vaccinia virus, wherein said extract is a protein free hygroscopic powder, has an ultraviolet adsorption max of 255–275 nm, and is positive for ninhydrin reaction.

10. A method as claimed in claim 9 wherein the inflammatory tissue is a skin tissue.

11. A method as claimed in claim 10 wherein the inflammatory tissue is a skin tissue of a mammal.

12. A method as claimed in claim 9 wherein the inflammatory tissue is rabbit skin.

13. A method as claimed in claim 9 wherein said extract is administered by injection.

14. A method as claimed in claim 9 wherein said extract is administered orally.

15. A method for inhibiting a decrease in trabecular connectivity and for inhibiting an increase in trabecular unconnectivity in a patient afflicted with osteoporosis caused by or accompanying a decrease in estrogen comprising administering to said patient a pharmaceutically effective amount of an extract from inflammatory tissue inoculated with vaccinia virus, wherein said extract is a protein free hygroscopic powder, has an ultraviolet adsorption max of 255–275 nm, and is positive for ninhydrin reaction.

16. A method as claimed in claim 15 wherein the inflammatory tissue is a skin tissue.

17. A method as claimed in claim 16 wherein the inflammatory tissue is a skin tissue of a mammal.

18. A method as claimed in claim 15 wherein the inflammatory tissue is rabbit skin.

19. A method as claimed in claim 15 wherein said extract is administered by injection.

20. A method as claimed in claim 15 wherein said extract is administered orally.

* * * * *